(12) United States Patent
Kim et al.

(10) Patent No.: US 8,594,409 B2
(45) Date of Patent: Nov. 26, 2013

(54) AUTOMATION METHOD FOR COMPUTERIZED TOMOGRAPHY IMAGE ANALYSIS USING AUTOMATED CALCULATION OF EVALUATION INDEX OF DEGREE OF THORACIC DEFORMATION BASED ON AUTOMATIC INITIALIZATION, AND RECORD MEDIUM AND APPARATUS

(75) Inventors: Sung Min Kim, Goyang-si (KR); Ho Chul Kim, Seoul (KR)

(73) Assignee: Dongguk University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/519,722

(22) PCT Filed: Feb. 9, 2012

(86) PCT No.: PCT/KR2012/000964
§ 371 (c)(1),
(2), (4) Date: Aug. 7, 2012

(87) PCT Pub. No.: WO2012/124897
PCT Pub. Date: Sep. 20, 2012

(65) Prior Publication Data
US 2012/0308110 A1 Dec. 6, 2012

(30) Foreign Application Priority Data
Mar. 14, 2011 (KR) .................. 10-2011-0022361

(51) Int. Cl.
*G06K 9/00* (2006.01)
(52) U.S. Cl.
USPC .................. 382/131; 382/199; 382/294
(58) Field of Classification Search
USPC .................. 382/128, 131, 199, 294
See application file for complete search history.

(56) References Cited

U.S. PATENT DOCUMENTS

| | | | |
|---|---|---|---|
| 6,766,043 B2 * | 7/2004 | Zeng et al. | 382/128 |
| 6,795,521 B2 * | 9/2004 | Hsu et al. | 378/4 |
| 7,397,934 B2 * | 7/2008 | Bloch et al. | 382/128 |
| 7,796,790 B2 * | 9/2010 | McNutt et al. | 382/128 |
| 8,073,226 B2 * | 12/2011 | Farag et al. | 382/131 |
| 2003/0035507 A1 * | 2/2003 | Hsu et al. | 378/4 |
| 2003/0099389 A1 * | 5/2003 | Zeng et al. | 382/131 |
| 2003/0216631 A1 * | 11/2003 | Bloch et al. | 600/407 |
| 2005/0207630 A1 * | 9/2005 | Chan et al. | 382/131 |
| 2009/0252395 A1 * | 10/2009 | Chan et al. | 382/131 |
| 2010/0189320 A1 * | 7/2010 | Dewaele | 382/128 |

FOREIGN PATENT DOCUMENTS

| | | | |
|---|---|---|---|
| JP | 2001-0086855 A | | 9/2001 |
| JP | 2003-523801 A | | 8/2003 |
| JP | 2005-199057 A | | 7/2005 |
| JP | 2007-061607 A | | 3/2007 |

* cited by examiner

*Primary Examiner* — John Strege
(74) *Attorney, Agent, or Firm* — The Webb Law Firm

(57) ABSTRACT

An automation method for CT image analysis for quantitatively analyzing the degree of thoracic deformation, and a record medium and apparatus are disclosed.

19 Claims, 8 Drawing Sheets

PRIOR ART

| | No. | h1 | h2 | Depression (h1/h2) | AR | AL | Asymmetry (AR/AL) |
|---|---|---|---|---|---|---|---|
|  | 01 | 201.5041 | 239.1072 | 0.8427 | 15545.4247 | 20753.4161 | 0.7491 |
|  | 02 | 205.9308 | 239.1072 | 0.8612 | 16185.9944 | 20907.9399 | 0.7742 |
|  | 03 | 210.2401 | 239.1072 | 0.8793 | 16861.9837 | 21005.9389 | 0.8027 |
|  | 04 | 214.3671 | 239.1072 | 0.8965 | 17513.9744 | 21094.9379 | 0.8302 |
|  | 05 | 218.3118 | 239.1072 | 0.9130 | 18127.9665 | 21187.9370 | 0.8556 |
|  | 06 | 222.1350 | 239.1072 | 0.9290 | 18721.9595 | 21279.9361 | 0.8798 |
|  | 07 | 225.7758 | 239.1072 | 0.9442 | 19290.9533 | 21362.9354 | 0.9030 |
|  | 08 | 229.2841 | 239.1072 | 0.9589 | 19833.9479 | 21448.9346 | 0.9247 |
|  | 09 | 232.6266 | 239.1072 | 0.9729 | 20352.9432 | 21528.9339 | 0.9454 |
|  | 10 | 235.9580 | 239.1072 | 0.9868 | 20859.9389 | 21617.9332 | 0.9649 |
|  | 11 | 239.1072 | 239.1072 | 1.0000 | 21345.9351 | 21695.9326 | 0.9839 |

| | No. | h1 | h2 | Depression (h1/h2) | AR | AL | Asymmetry (AR/AL) |
|---|---|---|---|---|---|---|---|
|  | 12 | 181.1349 | 217.3171 | 0.8335 | 19022.5122 | 13613.5358 | 1.3973 |
|  | 13 | 185.6819 | 217.3171 | 0.8544 | 19144.5118 | 14306.5309 | 1.3382 |
|  | 14 | 189.9360 | 217.3171 | 0.8740 | 19259.5114 | 14952.5270 | 1.2880 |
|  | 15 | 194.0078 | 217.3171 | 0.8927 | 19377.5110 | 15562.5238 | 1.2451 |
|  | 16 | 197.7923 | 217.3171 | 0.9102 | 19484.5107 | 16131.5211 | 1.2079 |
|  | 17 | 201.4221 | 217.3171 | 0.9269 | 19594.5104 | 16670.5189 | 1.1754 |
|  | 18 | 204.8862 | 217.3171 | 0.9428 | 19698.5101 | 17184.5170 | 1.1463 |
|  | 19 | 208.1735 | 217.3171 | 0.9579 | 19800.5098 | 17668.5154 | 1.1207 |
|  | 20 | 211.3447 | 217.3171 | 0.9725 | 19896.5096 | 18138.5140 | 1.0969 |
|  | 21 | 214.3558 | 217.3171 | 0.9864 | 19993.5094 | 18577.5128 | 1.0762 |
|  | 22 | 217.3171 | 217.3171 | 1.0000 | 20090.5092 | 19007.5117 | 1.0570 |

| | No. | h1 | h2 | Depression (h1/h2) | AR | AL | Asymmetry (AR/AL) |
|---|---|---|---|---|---|---|---|
|  | 23 | 204.0603 | 233.6128 | 0.8735 | 18421.1748 | 18413.1748 | 1.0004 |
|  | 24 | 207.8780 | 233.6128 | 0.8898 | 18755.1748 | 18758.1748 | 0.9998 |
|  | 25 | 211.4636 | 233.6128 | 0.9052 | 19068.1747 | 19081.1747 | 0.9993 |
|  | 26 | 214.8062 | 233.6128 | 0.9195 | 19360.1747 | 19381.1747 | 0.9989 |
|  | 27 | 217.9332 | 233.6128 | 0.9329 | 19631.1747 | 19664.1747 | 0.9983 |
|  | 28 | 220.9388 | 233.6128 | 0.9457 | 19893.1746 | 19934.1746 | 0.9979 |
|  | 29 | 223.6736 | 233.6128 | 0.9575 | 20130.1746 | 20179.1746 | 0.9976 |
|  | 30 | 226.3752 | 233.6128 | 0.9690 | 20362.1746 | 20423.1746 | 0.9970 |
|  | 31 | 228.8835 | 233.6128 | 0.9798 | 20582.1746 | 20645.1746 | 0.9969 |
|  | 32 | 231.3200 | 233.6128 | 0.9902 | 20793.1746 | 20863.1746 | 0.9966 |
|  | 33 | 233.6128 | 233.6128 | 1.0000 | 20991.1746 | 21067.1746 | 0.9964 |

AUTOMATION METHOD FOR COMPUTERIZED TOMOGRAPHY IMAGE ANALYSIS USING AUTOMATED CALCULATION OF EVALUATION INDEX OF DEGREE OF THORACIC DEFORMATION BASED ON AUTOMATIC INITIALIZATION, AND RECORD MEDIUM AND APPARATUS

CROSS-REFERENCE TO RELATED APPLICATION

This application claims priority to and the benefit of Korean Patent Application No. 10-2011-0022361, filed Mar. 14, 2011, the disclosure of which is incorporated herein by reference in its entirety.

BACKGROUND

1. Field of the Invention

The present invention relates to an automation method for computerized tomography (CT) image analysis using automated calculation of an evaluation index for quantitatively analyzing a degree of thoracic deformation based on automatic initialization, and a record medium and apparatus, and more particularly, to an automation method for CT image analysis and a record medium and apparatus, which completely automate an initialization operation for image segmentation by applying various image processing techniques, and thus automatically extract the internal boundary information of a thorax from a CT image and automatically calculate indexes for evaluating the degree of thoracic deformation of a funnel chest patient on the basis of the extracted information.

2. Discussion of Related Art

Evaluation preceding surgery for a degree of thoracic deformation of a funnel chest (pectus excavatum) patient is necessary for preparing a surgery, and evaluation succeeding the surgery is important to determine the result of the surgery.

Therefore, in order to establish a surgery plan for curing a funnel chest patient and analyze the result of the surgery before and after, various indexes such as a Haller index, a vertebral index, and a depression index for quantitatively expressing the degree of a thoracic deformation are being used in clinical trials.

Referring to FIG. 1, for example, a Haller index is defined as $a/c$ (i.e., Haller index=$a/c$), and a vertebral index is defined as $100*v/(v+c)$ (i.e., vertebral index=$100*v/(v+c)$). Here, "a" is the left and right length of a thorax, "c" is the distance between a sternum and a spine, and "v" is the length of a spine body.

A depression index, an asymmetry index, an eccentricity index, and an unbalance index are extracted by calculating an angle and a ratio of different lengths on the basis of the thorax information of FIG. 1 depending on the case and are used for a surgery of a funnel chest based on a Nuss surgery scheme.

Typically, the calculation of the indexes depends on a manual measurement scheme of manually analyzing the thoracic CT image of a patient, calculating several measurement values necessary for the calculation of the indexes and calculating the indexes. For this reason, time spent on measuring and calculating is long, and a large deviation of the calculated results occurs according to the measurers and measurement conditions.

Accordingly, it is required to automate the calculation of the indexes and thus shorten time spent on calculating and remove the deviation of the calculated results. Referring to FIG. 2, in the active contour model (ACM), a measurer such as an operating surgeon manually marks ten initial points around a region of interest (ROI), i.e., a thoracic boundary, in order to extract a boundary value of the ROI, and the marked points are interconnected by an interpolation scheme, thereby generating an initial contour line 210.

Furthermore, by performing a deformation operation of the ACM, that is, an image segmentation algorithm, a thorax internal boundary 220 is finally extracted from the initial contour line 210. The indexes that represent the degree of thoracic deformation are calculated with the extracted thorax internal boundary 220.

However, even in such a CT image analysis scheme, there is a limitation in that a measurer manually marks the initial points for image segmentation for a thoracic boundary, and thus finds the initial contour line 210 and extracts the thorax internal boundary 220. Also, a clinical doctor needs to understand relevant engineering technology and perform a practice operation to master the engineering technology in order to set accurate initial points.

SUMMARY OF THE INVENTION

The present invention is directed to providing an automation method for CT image analysis and a record medium and apparatus, which completely automate an initialization operation for image segmentation by applying various image processing techniques, and thus automatically extract the internal boundary information of a thorax from a CT image and automatically calculate the indexes for evaluating the degree of thoracic deformation of a funnel chest patient on the basis of the extracted information.

The present invention is also directed to providing an automation method for CT image analysis and a record medium and apparatus, which save time spent on measuring and enhance the accuracy and precision of measurement compared to a manual scheme by automating an initialization operation for image segmentation, thus maximizing the efficiency of work and clinical usability.

The present invention is also directed to providing an automation method for CT image analysis and a record medium and apparatus, which can be more effectively used in operating on a thorax deformation disease such as a funnel chest according to the new indexes based on an image processing technique by using the image processing technique including histogram analysis, point detection and object recognition for automating the initialization operation.

In addition to the aforesaid objects of the present invention, other features and advantages will be described in detail below to allow those skilled in the art to clearly understand the present invention.

One aspect of the present invention provides an automation method for computerized tomography (CT) image analysis for quantitatively analyzing a degree of thoracic deformation of a target patient on the basis of a thoracic CT image by using a CT image analysis unit including: receiving the thoracic CT image; horizontally aligning the thoracic CT image on the basis of boundary information on the lungs in the thoracic CT image; storing boundary information of each plurality of regions including the lungs on the basis of the horizontally aligned thoracic CT image; generating an edge map on the basis of the boundary information of each region which has been obtained from the thoracic CT image; generating a GVF field corresponding to the edge map; extracting a contour line, which connects a boundary of the left and right lungs and a boundary for bones, to set an initial contour line which connects the boundary for the lungs and the boundary for the bones on the basis of the boundary information of each region, the bones including a sternum, a spine, and ribs;

extracting a thorax internal boundary by performing an ACM deformation such that the initial contour line which connects the boundary for the lungs and the boundary for the bones approximates an internal thorax boundary based on the edge map, according to the GVF field; and analyzing the thorax internal boundary to calculate a plurality of indexes for a degree of thoracic deformation based on a signature analysis technique.

Based on the signature analysis technique, calculating a plurality of indexes may include: extracting a first average line, a second average line, a center line, a first area, and a second area from the thorax internal boundary; calculating an index for depression (DI) evaluation from the first average line and the second average line; and calculating an index for asymmetry (AI) evaluation from the first area and the second area.

The index for depression evaluation may be calculated as expressed in the following equation, $$DI = \text{first average line/second average line}.$$

The index for asymmetry evaluation may be calculated as expressed in the following equation, $$AI = \text{first area/second area}.$$

The horizontal aligning of the thoracic CT image may include: detecting a lower end point of the left lung and a lower end point of the right lung from the boundary information of the lungs; and calculating an angle and direction of a line segment which are inclined with respect to a reference horizontal line, and rotating the thoracic CT image for the line segment to be parallel to the reference horizontal line, the line segment connecting the lower end point of the left lung and the lower end point of the right lung.

A histogram distribution representing a distribution of each region by brightness may be analyzed, and the boundary for the lungs may be calculated from a distribution of an image for threshold brightness corresponding to the lungs.

The storing of boundary information may include analyzing a histogram distribution, which represents a distribution of each region by brightness, to calculate and store boundary information on a corresponding region which includes the lungs, the sternum, the spine, and the ribs.

The generating of an edge map includes: generating the edge map, which includes the boundary for the lungs and the boundary for the bones including the sternum, the spine, and the ribs, on the basis of the boundary information of each region which has been obtained from the thoracic CT image.

The setting of the initial contour line may include: extracting a sternum lower end point from a boundary for the sternum among the boundary information, extracting a first right point and a first left point from the sternum lower end point, the first right and left points being closest to the boundary for the lungs among the boundary information, and setting an initial upper end contour line which sequentially connects a plurality of points including the first left point, the sternum lower end point, and the first right point; extracting a spine upper end point from a boundary for the spine among the boundary information, extracting a second right point and a second left point from the spine upper end point, the second right and left points being closest to the boundary for the lungs among the boundary information, and setting an initial lower end contour line which sequentially connects a plurality of points including the second left point, the spine upper end point, and the second right point; and connecting the boundary for the lungs, the initial upper end contour line, and the initial lower end contour line as one to finally form the initial contour line.

Another aspect of the present invention provides a computer-readable record medium storing a program for executing any one of the methods.

Still another aspect of the present invention provides an automation apparatus for computerized tomography (CT) image analysis for analyzing a degree of thoracic deformation of a target patient on the basis of a thoracic CT image including: an alignment unit configured to horizontally align the thoracic CT image on the basis of boundary information on the lungs in the received thoracic CT image; a storage unit configured to store boundary information of each plurality of regions including the lungs on the basis of the horizontally aligned thoracic CT image; an edge map generation unit configured to generate an edge map on the basis of the boundary information of each region which has been obtained from the thoracic CT image; a GVF field generation unit configured to generate a GVF field corresponding to the edge map; an initial contour line setting unit configured to extract a contour line, which connects a boundary of left and right lungs and a boundary for bones, to set an initial contour line which connects the boundary for the lungs and the boundary for the bones on the basis of the boundary information, the bones including a sternum, a spine, and ribs; a thorax internal boundary extraction unit configured to extract a thorax internal boundary by performing an ACM deformation such that the initial contour line which connects the boundary for the lungs and the boundary for the bones approximates an internal thorax boundary based on the edge map according to the GVF field; and an analysis unit configured to analyze the thorax internal boundary to calculate a plurality of indexes for a degree of thoracic deformation based on a signature analysis technique.

BRIEF DESCRIPTION OF THE DRAWINGS

The above and other objects, features and advantages of the present invention will become more apparent to those of ordinary skill in the art by describing in detail the exemplary embodiments thereof with reference to the attached drawings in which.

DETAILED DESCRIPTION OF THE EXEMPLARY EMBODIMENTS

Figure 1:
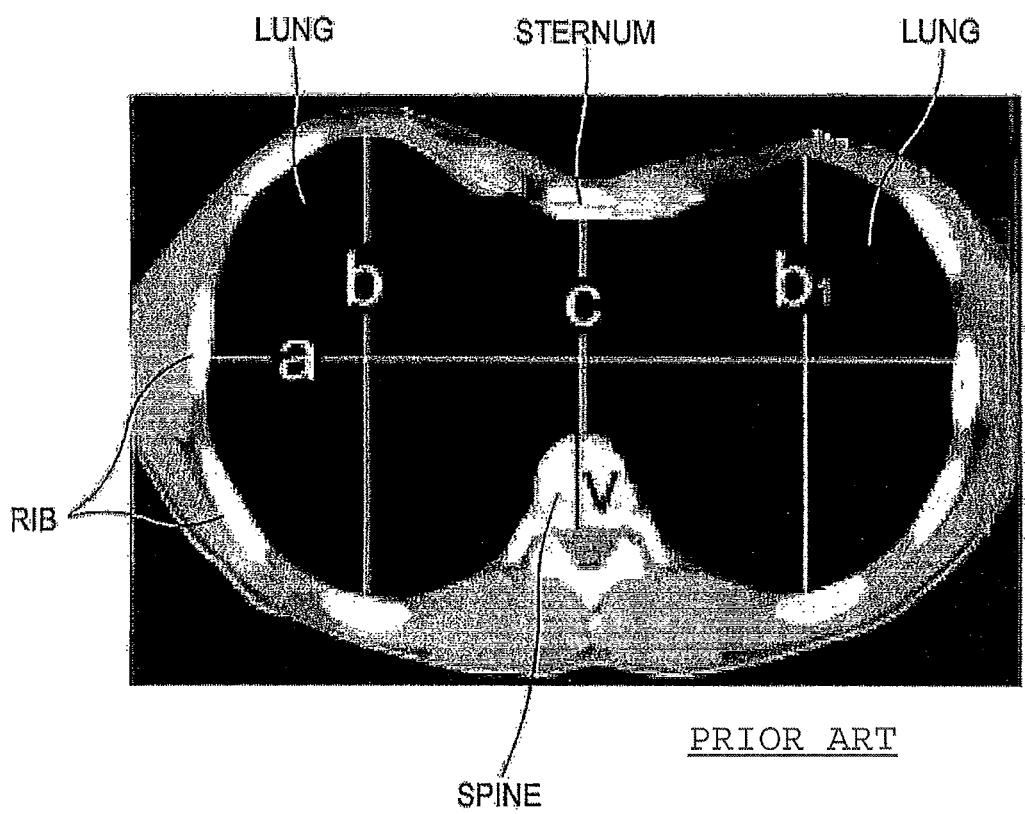
FIG. 1 illustrates a CT image for describing general indexes for evaluating the degree of thoracic deformation.
Figure 2:
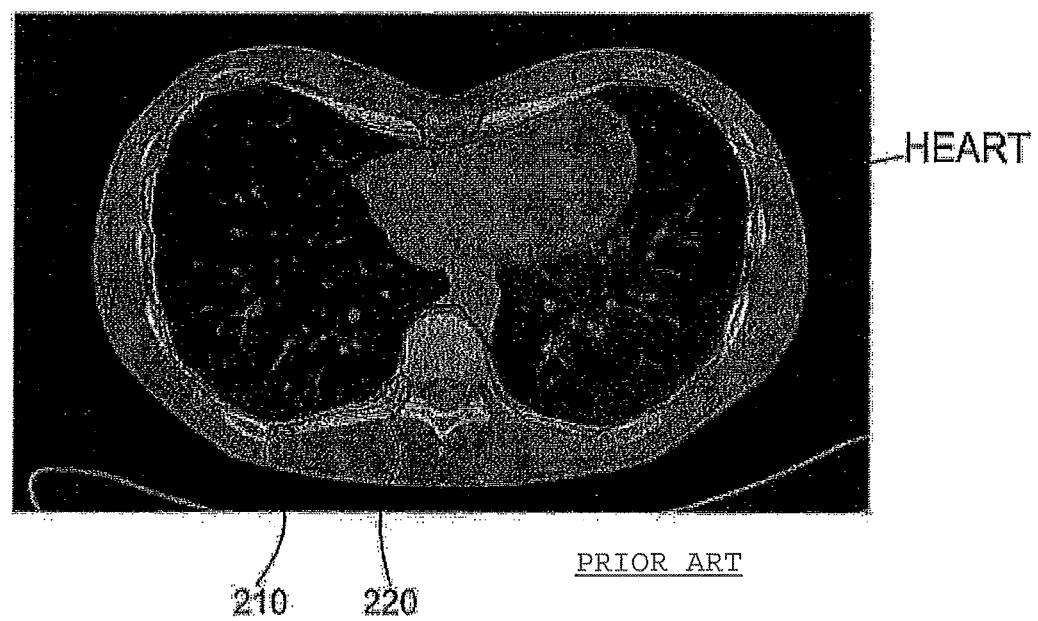
FIG. 2 is a diagram for describing the extraction of a thorax internal boundary with the deformation of the ACM which is an initialization operation performed manually and is an image segmentation algorithm.

Hereinafter, the exemplary embodiments of the present invention will be described in detail. In the drawings, the sizes or shapes of elements may be exaggerated for clarity and convenience of the description. Moreover, the terms used henceforth have been defined in consideration of the functions of the present invention and may be altered according to the intent of a user or operator, or for conventional practice. Therefore, the terms should be defined on the basis of the entire content of this specification.

Furthermore, the present invention may be embodied in many different forms and should not be construed as being limited to the embodiments set forth herein; rather, that alternate embodiments included in other retrogressive inventions or falling within the spirit and scope of the present disclosure can easily be derived through adding, altering, and changing, and will fully convey the concept of the invention to those skilled in the art.

Figure 3:
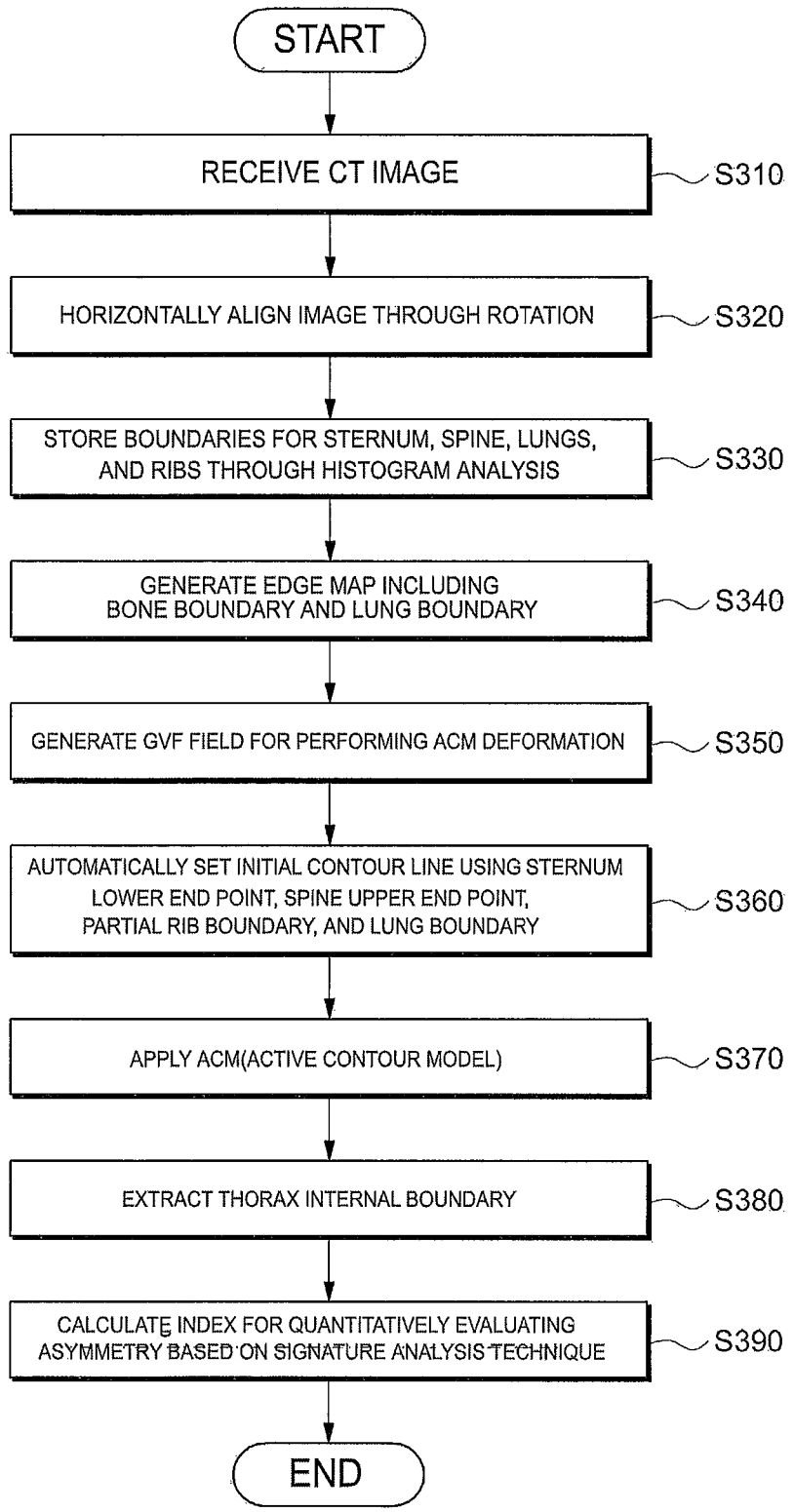
FIG. 3 is a diagram for describing an automation method for CT image analysis using an automatic initialization operation according to an embodiment of the present invention.

FIG. 3 is a diagram for describing an automation method for CT image analysis using an automatic initialization operation according to an embodiment of the present invention.

Referring to FIG. 3, the automation method for CT image analysis according to an embodiment of the present invention includes: operation S310 of receiving a thoracic CT image; operation S320 of horizontally aligning the thoracic CT image on the basis of boundary information on the lungs in the thoracic CT image; operation S330 of storing boundary information of each region (organ and tissue) including the lungs on the basis of the horizontally aligned thoracic CT image; operation S340 of generating an edge map for extracting an accurate thorax internal boundary on the basis of the boundary information of each region that has been obtained from the thoracic CT image; operation S350 of generating a gradient vector flow field (GVF) corresponding to the edge map for performing an ACM deformation; operation S360 of extracting a contour line which connects a boundary (value) of the left and right lungs and a boundary (value) of the bones (including a spine, ribs, and a sternum) on the basis of the boundary information, and setting an initial contour line which connects boundaries of the lungs and bones; operation S380 of performing the ACM deformation in order for the initial contour line (which connects the boundaries of the lungs and bones) to approximate an internal thorax boundary based on the edge map according to the GVF field; operation S380 of extracting a thorax internal boundary by performing operation S370; and operation S390 of analyzing the thorax internal boundary on the basis of the extracted thorax internal boundary (value) in a signature analysis technique to thereby calculate the indexes (DI and AI) for the degree of thoracic deformation.

Each operation of the automation method for CT image analysis according to an embodiment of the present invention may be implemented as hardware, software, or a combination thereof. The automation method for CT image analysis according to an embodiment of the present invention may be implemented with a CT image analysis apparatus using a computer and implemented in a type of digital information such as computer-readable software, thereby allowing each function to be realized. The automation method for CT image analysis according to an embodiment of the present invention may receive a thoracic CT image from a CT apparatus to process the CT image, and thus may be used to analyze the degree of thoracic deformation of a target patient.

Hereinafter, each operation of the automation method for CT image analysis according to an embodiment of the present invention will be described in detail.

Figure 4:
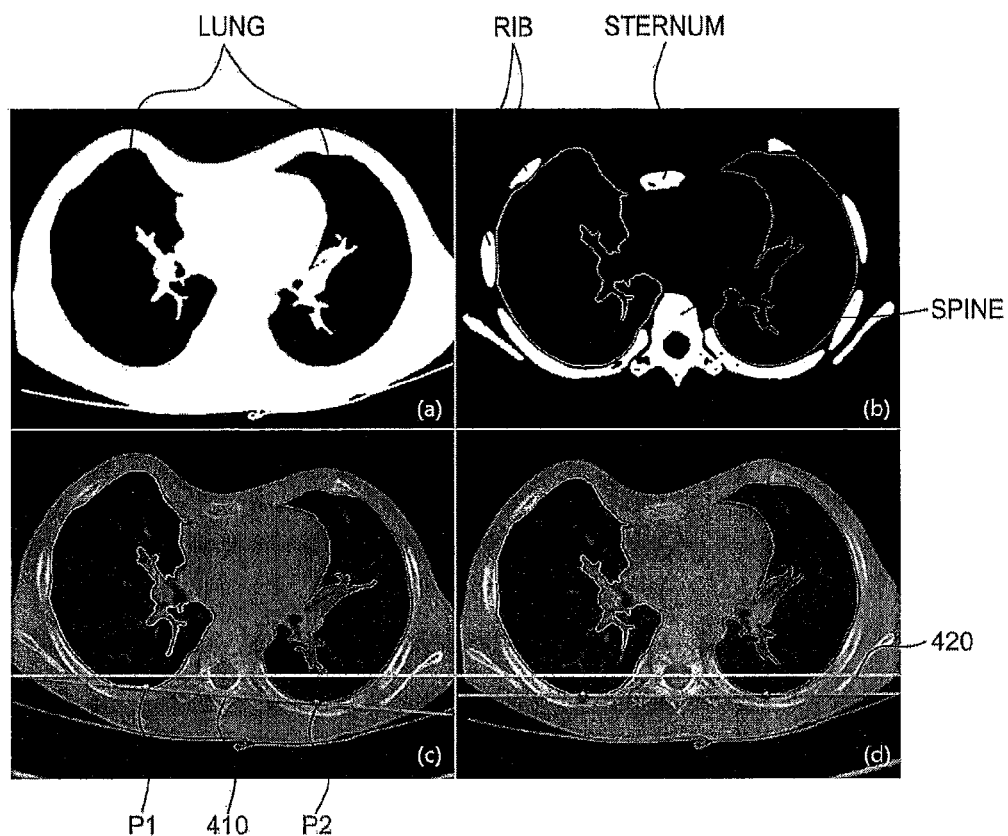
FIG. 4 is a diagram for describing the boundary registration of each region and horizontal alignment of a CT image in the automation method for CT image analysis according to an embodiment of the present invention.

FIG. 4 is a diagram for describing the boundary registration of each region and horizontal alignment of a CT image in the automation method for CT image analysis according to an embodiment of the present invention.

First, when a thoracic CT image of a target patient is received from the CT apparatus, a CT image analysis means (For example, an automation apparatus for CT image analysis) may horizontally align the thoracic CT image on the basis of boundary information on lungs which is included in the thoracic CT image in operation S320 (See FIG. 3).

In a CT image received from the CT apparatus, an ROI (including a chest-wall inner boundary) in the image is often inclined without being horizontally aligned according to the posture of a patient and ambient conditions. Therefore, to accurately calculate an index to be measured, the left and right sides of the thorax may be horizontally disposed in a CT image. Accordingly, the inclinations of the left and right lungs are checked from the received CT image, and then horizontal adjustment is performed by rotating the entire CT image.

For example, first, an alignment means may analyze a histogram distribution that represents the distribution of each region by brightness, and calculate boundary information on the lungs from the distribution of an image for threshold brightness corresponding to the lungs. In a CT image, regions such as lungs, a sternum, a spine, and ribs may be distributed at different brightnesses. Therefore, a histogram distribution (For example, a Hounsfield unit (HU)) that represents the distribution of regions respectively corresponding to certain brightness digital values (For example, 0 to 255) may be calculated, and boundary information (For example, coordinate values on a screen) on each of the regions may be calculated from the distribution of an image corresponding to one or more threshold brightnesses.

Only boundary information on the lungs may be calculated to be differentiated from the other regions (bones such as a sternum, a spine, and ribs, or a heart, (See (b) of FIG. 4), through the histogram analysis. Therefore, the alignment means may first detect a lower end point P1 of a left lung and a lower end point P2 of a right lung from the calculated boundary information on the lungs (See (a) of FIG. 4). Here, P1 is a point that is disposed at the lowermost portion in a vertical direction in the left lung, and P2 is a point that is disposed at the lowermost portion in a vertical direction in the right lung.

Moreover, an angle and direction (upward or downward) of a line segment 410 (which connects the lower end point P1 of the left lung and the lower end point P2 of the right lung) that are inclined with respect to a reference horizontal line 420 may be calculated, and the entire thoracic CT image may be rotated in order for the line segment 410 to be parallel to the reference horizontal line 420 according to the calculated results.

When the horizontal alignment is performed, a storage means may store the boundary information of each region including the lungs on the basis of the horizontally aligned thoracic CT image in operation S330 (See FIG. 3). For the horizontally aligned CT image, the boundary information on each region (including lungs, a sternum, a spine, and ribs) may be calculated and stored by analyzing the histogram distribution that represents the distribution of each region by brightness. As described above, the ROIs such as lungs, a sternum, a spine, and ribs have different HU values, and thus, the boundary information on each region may be automatically extracted on the basis of the different HU values and stored in the storage means (For example, a memory)

Figure 5:
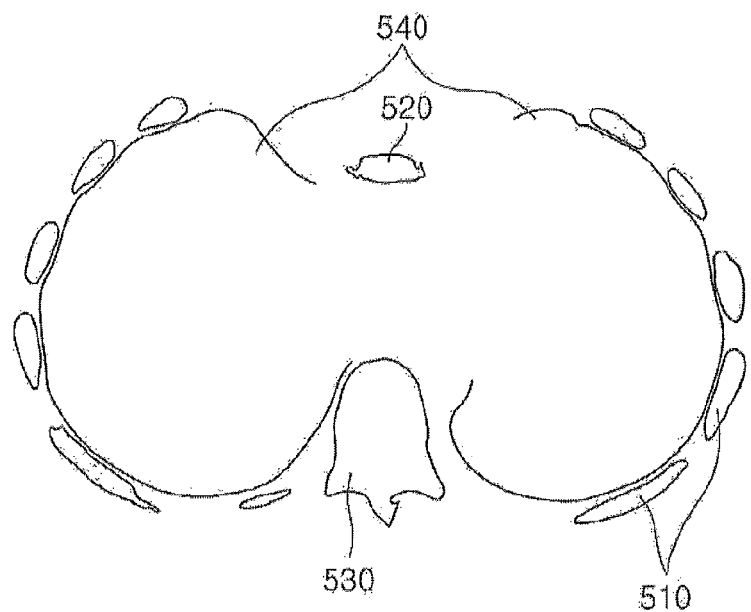
FIG. 5 is a diagram for describing an edge map in the automation method for CT image analysis according to an embodiment of the present invention.

FIG. 5 is a diagram for describing an edge map in the automation method for CT image analysis according to an embodiment of the present invention.

When all operations S310 to S330 for the preprocessing of the CT image are completed in order to extract a thorax internal boundary from the preprocessed CT image, as illustrated in FIG. 5, a CT image analysis means generate the edge map in operation S340 (See FIG. 3), and generate the GVF field in operation S350 (See FIG. 3). An edge map generation means may generate the edge map on the basis of the boundary information of each region that has been stored in operation S330 (See FIG. 3), and a GVF field generation means may generate the GVF field corresponding to the edge map. As illustrated in FIG. 5, the edge map is a map that includes a plurality of boundaries 510, 520 and 530 for bones including a sternum, a spine, and ribs.

As will be described below in detail, the automation method includes performing the ACM deformation to calculate the thorax internal boundary (value) in operation S370. To this end, the setting of the edge map, GVF field, and initial points (in the present invention, the initial contour line that connects the boundary value for the left and right lungs and the boundary value for one or some of the sternum, spine, and ribs on the basis of the extracted boundary information) is required. In the present invention, the setting is completely automated, and thus indexes for evaluating the degree of thoracic deformation of a funnel chest patient may also be calculated automatically by the signature analysis technique.

Figure 6:
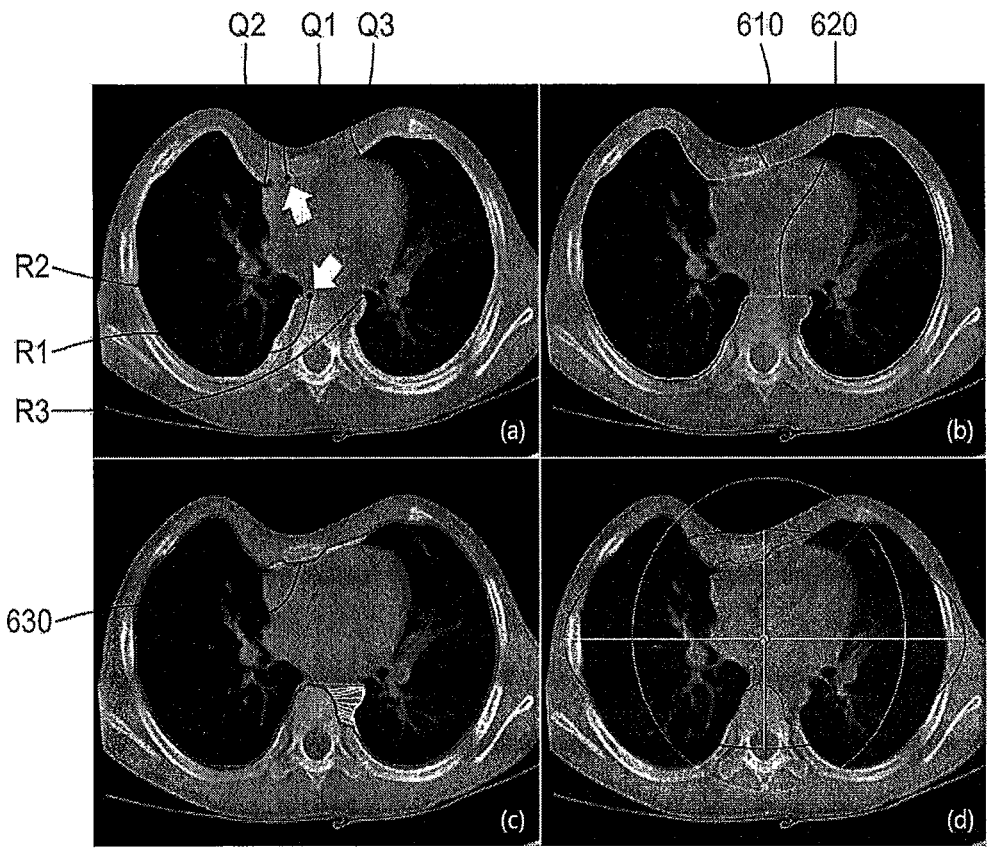
FIG. 6 is a diagram for describing the calculation of the indexes for quantitatively evaluating the degree of thoracic deformation and the extraction of a thorax internal boundary according to the deformation operation of the ACM which is an image segmentation algorithm using a completely automated initialization method in the automation method for CT image analysis according to an embodiment of the present invention.

FIG. 6 is a diagram for describing the calculation of the indexes for quantitatively evaluating the degree of thoracic deformation and the extraction of a thorax internal boundary according to the deformation operation of the ACM which is an image segmentation algorithm using a completely automated initialization method in the automation method for CT image analysis according to an embodiment of the present invention.

As described above, after the edge map is generated and the GVF field is generated, an initial contour setting means may set a plurality of initial contour lines 610 and 620 for the ACM deformation on the basis of the boundary information (including the lungs, sternum, spine, and ribs) of each region in operation S360 (See FIG. 3). On the basis of the boundary information on the lungs among the boundary information (including the lungs, sternum, spine, and ribs) of each region, the initial contour setting means may extract the contour lines 610 and 620, which connect the boundary for the left lung and the boundary for the right lung, to set an initial contour line that connects a boundary for the lungs and the bones.

For example, the initial contour setting means may extract a sternum lower end point Q1 from the boundary information (including the lungs, sternum, spine, and ribs) of each region, extract a left point Q2 and a right point Q3 from the sternum lower end point Q1, the left point Q2 and the right point Q3 being closest to the boundary for the lungs among the boundary information sequentially connect the left point Q2, the sternum lower end point Q1, and the right point Q3, and thus set the initial upper end contour line 610 that is connected to the boundary of the lungs at an upper portion. Here, to set a more accurate contour line, the initial contour setting means may set the initial upper end contour line 610 that connects corresponding points by further using the other points (position coordinate values) between the left point Q2 and the right point Q3 in addition to the left point Q2 and the right point Q3.

Similar to this, the initial contour setting means may extract a spine upper end point R1 from the boundary for the spine among the boundary information (including the lungs, sternum, spine, and ribs) of each region, extract a left point R2 and a right point R3 from the spine upper end point R1, the left point R2 and the right point R3 being closest to the boundary for the lungs among the boundary information sequentially connect the left point R2, the spine upper end point R1, and the right point R3, and thus set the initial lower end contour line 620 that is connected to the boundary of the lungs at a lower portion. Here, to set a more accurate contour line, the initial contour setting means may set the initial lower end contour line 620 that connects corresponding points by further using the other points (position coordinate values) between the left point R2 and the right point R3, in addition to the left point R2 and the right point R3.

In this way, when the initial upper end contour line 610 and the initial lower end contour line 620 are set, an initial contour line having one curve shape that connects the boundaries for the lungs and the bones (sternum, spine, and ribs) may be formed by finally connecting the initial upper end contour line 610, the initial lower end contour line 620, and the boundary for the lungs as one.

Figure 7:
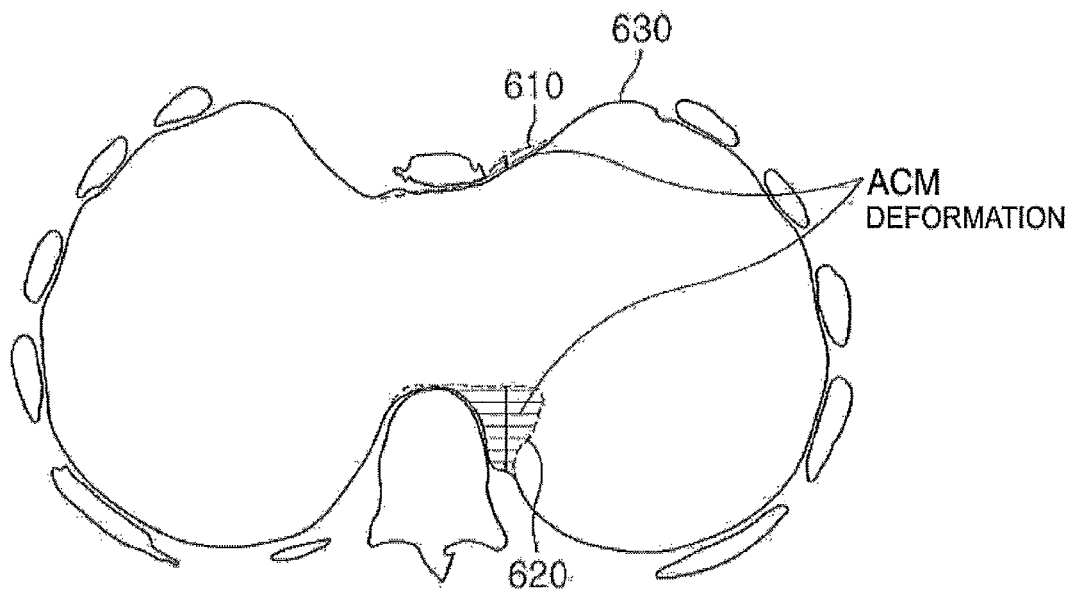
FIG. 7 is a diagram for describing the deformation operation of the ACM in the automation method for CT image analysis according to an embodiment of the present invention.

FIG. 7 is a diagram for describing a deformation operation in which the ACM that is a type of the image segmentation algorithm extracts the internal boundary value of the thorax from the initial contour line in the automation method for CT image analysis according to an embodiment of the present invention.

As described above, the initial contour line (contour line that connects the boundaries from the lungs and the bones) including the initial upper end contour line 610, the initial lower end contour line 620, and the boundary (value) for the lungs is set, and then a thorax internal boundary extraction means perform the ACM deformation according to the GVF field (which has been generated in operation S350) such that the initial contour line (which has been generated in operation S340) including the initial upper end contour line 610 and the initial lower end contour line 620 (which connect the boundaries for the lungs and the bones) approximates the internal thorax boundary based on the edge map, thereby extracting the thorax internal boundary 630 in operation S370 (See FIG. 3).

Referring to FIG. 7, as is well known, the ACM deformation is a numerical analysis scheme that allows a start point (i.e., the initial contour line including the initial upper end contour line 610 and the initial lower end contour line 620 which are connected to the boundary for the lungs) to approximate the thorax internal boundary based on the edge map. The ACM deformation finds one curve (contour line) that allows a boundary value of the initial contour line (including the initial upper end contour line 610 and the initial lower end contour line 620 which are connected to the boundary for the lungs) to maximally approximate an edge (boundary) for thorax internal bones such as the sternum, the spine, and the ribs.

A boundary for the lungs before the setting of the initial contour line (including the initial upper end contour line 610, the initial lower end contour line 620, and a partial boundary of the lungs) is stored as information approximate to the edges of the sternum, spine, and ribs in operation S330 (See FIG. 3).

Therefore, as illustrated in FIG. 7, when an initial contour line (including one or some of the boundary values of the lungs, the initial upper end contour line 610, and the initial lower end contour line 620) that is formed adjacent to the thorax internal boundary is set as an initialization value of the ACM that is the image segmentation algorithm, a thorax internal boundary 630 is found by performing the ACM deformation. The ACM deformation can be obtained from prior materials, and thus, its detailed description is not provided herein.

Figure 8:
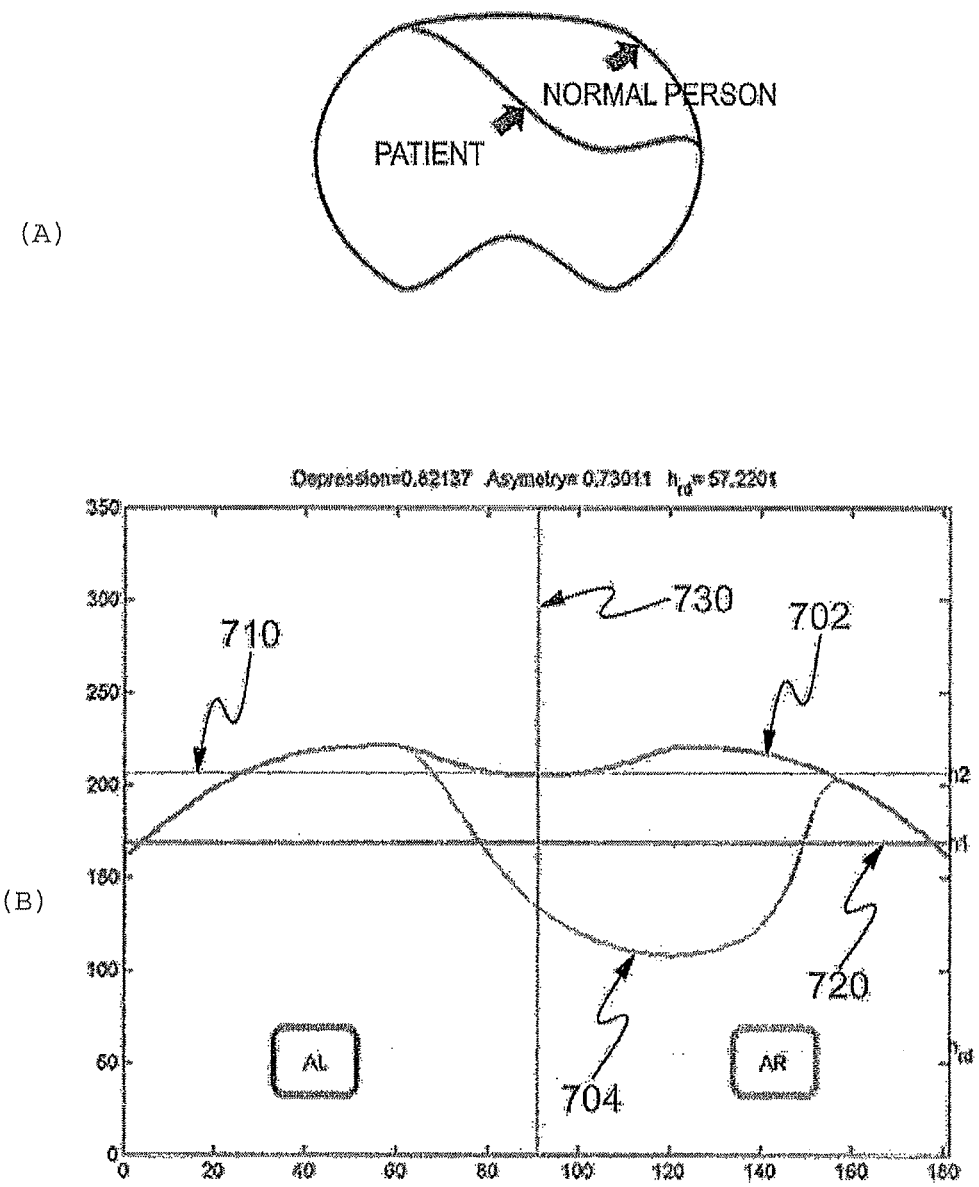
FIGS. 8(A) and 8(B) are diagrams for describing the indexes for the degree of thoracic deformation according to an embodiment of the present invention.

FIGS. 8(A) and 8(B) are diagrams for describing indexes for the degree of thoracic deformation according to an embodiment of the present invention.

As described above, when the thorax internal boundary 630 is extracted by the ACM, that is, the image segmentation algorithm, an analysis means analyzes the thorax internal boundary 630 in the signature analysis technique to calculate an index for diagnosing and evaluating the degree of thoracic deformation of a funnel chest patient in operation S390 (see FIG. 3).

First, as shown in FIG. 8B, the automation method includes extracting a first average line 720, a second average line 710, a center line 730, a first area AR, and a second area AL from a thorax internal boundary between a normal person and a thorax malformation patient (see FIG. 8A), based on the signature analysis technique.

The signature analysis technique is a technique of representing a two-dimensional (2D) thorax internal boundary as a one-dimensional (1D) function. As shown in FIG. 8B, a distance from an internal center point of the thorax to a thorax internal boundary is represented to correspond to an angle (FIG. 8B only shows a rear portion of the thorax, i.e., a forward portion of the thorax other than a back, i.e., a signature (0 C degree to 180 C degrees) for a chest), and thus, a signature 704 for the thorax malformation patient and a signature 702 for the normal person may be shown in order for the degree of thoracic deformation to be determined easier than a thorax internal boundary.

That is, in the signature 704 for the patient, a distance from the internal center point of the thorax to the thorax internal boundary is rapidly reduced at 90 C degrees to 180 C degrees, but the signature 702 is shown to be symmetric with respect to 90 C degrees. Accordingly, an index for diagnosing and evaluating the degree of thoracic deformation can be calculated easily.

Here, the first average line 720 is a theoretical line parallel to the X-axis that is set in order for the first average line 720 to be equal to the sum of all peak areas and valley areas in the signature 704, and when it is assumed that the thorax malformation patient is a normal person, the second average line 710 is a theoretical line parallel to the X-axis that is set in order for the second average line 710 to be equal to the sum of all peak areas and valley areas in the signature 704.

The center line 730 represents a chest center of the thorax malformation patient or normal person, i.e., the center line of the signature. The first area AR is an area (i.e., an area between 90 C degrees and 180 C degrees on the X axis) that is formed rightward from the center line 730 within an area which is surrounded by the X-axis, the Y-axis, the signatures 702 and 704, and the center line 730. The second area AL is an area (i.e., an area between 0 C degree and 90 C degrees on the X axis) that is formed leftward from the center line 730, within the area which is surrounded by the X-axis, the Y-axis, the signatures 702 and 704, and the center line 730.

In this way, when the first average line 720, the second average line 710, the center line 730, the first area AR, and the second area AL have been extracted from the thorax internal boundary 630 by the signature analysis technique, the analysis means may calculate an index DI for depression evaluation from the first average line 720 and the second average line 710, and calculate an index AI for asymmetry evaluation from the first area AR and the second area AL.

Specifically, the index for depression evaluation may be calculated with an equation "DI=first average line/second average line," and the index for asymmetry evaluation may be calculated with an equation "AI=first area/second area." As the index for depression evaluation and the index for asymmetry evaluation approach 1, the indexes denote a thorax close to that of a normal person.

According to the present invention, the extraction of the indexes DI and AI, the deformation and asymmetry of a thorax are simultaneously analyzed by applying a relatively uncomplicated and simple algorithm, and thus, the automation method can be more effectively used in operating on a thorax deformation disease such as a funnel chest.

Figure 9:
FIGS. 9 to 11 are diagrams for describing an index calculation result according to an embodiment of the present invention.
Figure 9:
Figure 9:
Figure 9:
Figure 9:
Figure 9:
Figure 9:
Figure 9:
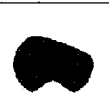
Figure 9:
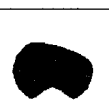
Figure 9:
Figure 9:
Figure 10:
Figure 10:
Figure 10:
Figure 10:
Figure 10:
Figure 10:
Figure 10:
Figure 10:
Figure 10:
Figure 10:
Figure 10:
Figure 11:
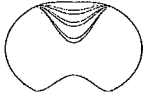
Figure 11:
Figure 11:
Figure 11:
Figure 11:
Figure 11:
Figure 11:
Figure 11:
Figure 11:
Figure 11:
Figure 11:

FIGS. 9 to 11 are diagrams for describing an index calculation result according to an embodiment of the present invention.

Referring to FIG. 9, indexes for the degree of thoracic deformation are calculated for a patient whose thorax is indented on a right side, and according to the calculated index result, when the right side of the thorax is deeply indented (i.e., progressively closer to the top of FIG. 10), the index for depression evaluation and the index for asymmetry evaluation become farther away from 1, but when the right and left of the thorax are symmetric (i.e., progressively closer to the bottom of FIG. 10), the index for depression evaluation and the index for asymmetry evaluation approach 1.

Referring to FIG. 10, indexes for the degree of thoracic deformation are calculated for a patient whose thorax is indented on a left side, and according to the calculated index result, when the left side of the thorax is deeply indented (i.e., progressively closer to the top of FIG. 11), the index for depression evaluation and the index for asymmetry evaluation become farther away from 1, but when the right and left of the thorax are symmetric (i.e., progressively closer to the bottom of FIG. 11), the index for depression evaluation and the index for asymmetry evaluation approach 1.

Referring to FIG. 11, the asymmetry of the thorax is not shown, and thus, the index for asymmetry evaluation is shown as close to 1. Also, when the center portion of the thorax is deeply indented (i.e., progressively closer to the top of FIG. 12), the index for depression evaluation becomes farther away from 1, but when the thorax is not indented (i.e., progressively closer to the bottom of FIG. 12), the index for depression evaluation and the index for asymmetry evaluation approach 1.

As described above with reference to FIGS. 9 to 11, the present invention applies a relatively uncomplicated and simple algorithm for extracting the indexes DI and AI, and analyzes the deformation and asymmetry of a thorax simultaneously. Accordingly, the present invention can be more effectively used for a thorax deformation disease such as a funnel chest.

As described above, the automation method for CT image analysis according to an embodiment of the present invention includes extracting the new indexes DI and AI using the image processing technique including histogram analysis, point detection, and object recognition for automating the initialization operation, and thus can save time spent on measuring and enhance the accuracy and precision of measurement compared to a manual scheme, thus maximizing the efficiency of work and clinical usability. Accordingly, clinical doctors can more easily and quickly diagnose and evaluate the degree of thoracic deformation of a funnel chest patient, and more effectively use the automation method in operating on a funnel chest.

Moreover, with the extraction of the new indexes DI and AI, the present invention simultaneously analyzes the deformation and asymmetry of a thorax by applying a relatively uncomplicated and simple algorithm, and thus can be more effectively used in a thorax deformation disease such as a funnel chest.

The present invention can be implemented as computer readable codes in a computer readable record medium. The computer readable record medium includes all types of record media in which computer readable data is stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network in which computer readable codes may be stored and executed in a distributed manner.

The automation method for CT image analysis according to an embodiment of the present invention completely automates an initialization operation for image segmentation by applying various image processing techniques, and thus automatically extracts the internal boundary information of a thorax from a CT image and automatically calculates indexes for evaluating the degree of thoracic deformation of a funnel chest patient on the basis of the extracted information. Also, by automating an initialization operation for image segmentation, the automation method saves time spent on measuring and enhances the accuracy and precision of measurement compared to a manual scheme, thus maximizing the efficiency of work and clinical usability.

Furthermore, by using the image processing technique including histogram analysis, point detection, and object recognition for automating the initialization operation, the automation method can be more effectively used in operating on a thorax deformation disease such as a funnel chest according to new indexes DI and AI based on an image processing technique.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. An automation method for computerized tomography (CT) image analysis for quantitatively analyzing a degree of thoracic deformation of a target patient on the basis of a thoracic CT image using a CT image analysis unit, the automation method comprising:
   receiving the thoracic CT image;
   horizontally aligning the thoracic CT image on the basis of boundary information on the lungs in the thoracic CT image;
   storing boundary information of each plurality of regions comprising the lungs on the basis of the horizontally aligned thoracic CT image;
   generating an edge map on the basis of the boundary information of each region which has been obtained from the thoracic CT image;
   generating a GVF field corresponding to the edge map;
   extracting a contour line, which connects a boundary of left and right lungs and a boundary for bones, to set an initial contour line which connects the boundary for the lungs and the boundary for the bones on the basis of the boundary information of each region, the bones comprising a sternum, a spine, and ribs;
   extracting a thorax internal boundary by performing an ACM deformation such that the initial contour line which connects the boundary for the lungs and the boundary for the bones approximates an internal thorax boundary based on the edge map, according to the GVF field; and
   analyzing the thorax internal boundary to calculate a plurality of indexes for a degree of thoracic deformation based on a signature analysis technique.

2. The automation method of claim 1, wherein the calculating the plurality of indexes comprises:
   based on the signature analysis technique,
   extracting a first average line, a second average line, a center line, a first area, and a second area from the thorax internal boundary;
   calculating an index (DI) for depression evaluation from the first average line and the second average line; and
   calculating an index (AI) for asymmetry evaluation from the first area and the second area.

3. The automation method of claim 2, wherein the index for depression evaluation is calculated as expressed in the following equation, $$DI = \text{first average line/second average line}.$$

4. The automation method of claim 2, wherein the index for asymmetry evaluation is calculated as expressed in the following equation, $$AI = \text{first area/second area}.$$

5. The automation method of claim 1, wherein the horizontal aligning of the thoracic CT image comprises:
   detecting a lower end point of the left lung and a lower end point of the right lung from the boundary information on the lungs; and
   calculating an angle and direction of a line segment which are inclined with respect to a reference horizontal line, and rotating the thoracic CT image for the line segment to be parallel to the reference horizontal line, the line segment connecting the lower end point of the left lung and the lower end point of the right lung.

6. The automation method of claim 5, wherein a histogram distribution representing a distribution of each region by brightness is analyzed, and the boundary for the lungs is calculated from a distribution of an image for threshold brightness corresponding to the lungs.

7. The automation method of claim 1, wherein the storing of boundary information comprises analyzing a histogram distribution, which represents a distribution of each region by brightness, to calculate and store boundary information on a corresponding region which comprises the lungs, the sternum, the spine, and the ribs.

8. The automation method of claim 1, wherein the generating of an edge map comprises generating the edge map which comprises the boundary for the lungs and the boundary for the bones comprising the sternum, the spine, and the ribs on the basis of the boundary information of each region which has been obtained from the thoracic CT image.

9. The automation method of claim 1, wherein the setting of the initial contour line comprises:
   extracting a sternum lower end point from a boundary for the sternum among the boundary information, extracting a first right point and a first left point from the sternum lower end point, the first right and left points being closest to the boundary for the lungs among the boundary information, and setting an initial upper end contour line which sequentially connects a plurality of points comprising the first left point, the sternum lower end point, and the first right point;

extracting a spine upper end point from a boundary for the spine among the boundary information, extracting a second right point and a second left point from the spine upper end point, the second right and left points being closest to the boundary for the lungs among the boundary information, and setting an initial lower end contour line which sequentially connects a plurality of points comprising the second left point, the spine upper end point, and the second right point; and connecting the boundary for the lungs, the initial upper end contour line, and the initial lower end contour line as one to finally form the initial contour line.

10. A non-transitory computer-readable record medium storing a program for executing the method defined in claim 1.

11. An automation apparatus for computerized tomography (CT) image analysis for analyzing a degree of thoracic deformation of a target patient on the basis of a thoracic CT image, the automation apparatus comprising:

an alignment unit configured to horizontally align the thoracic CT image on the basis of boundary information on lungs in the received thoracic CT image;

a storage unit configured to store boundary information of each plurality of regions comprising the lungs on the basis of the horizontally aligned thoracic CT image;

an edge map generation unit configured to generate an edge map on the basis of the boundary information of each region which has been obtained from the thoracic CT image;

a GVF field generation unit configured to generate a GVF field corresponding to the edge map;

an initial contour line setting unit configured to extract a contour line, which connects a boundary of left and right lungs and a boundary for bones, to set an initial contour line which connects the boundary for the lungs and the boundary for the bones on the basis of the boundary information, the bones comprising a sternum, a spine, and ribs;

a thorax internal boundary extraction unit configured to extract a thorax internal boundary by performing an ACM deformation such that the initial contour line which connects the boundary for the lungs and the boundary for the bones approximates an internal thorax boundary based on the edge map according to the GVF field; and an analysis unit configured to analyze the thorax internal boundary to calculate a plurality of indexes for a degree of thoracic deformation based on a signature analysis technique.

12. A non-transitory computer-readable record medium storing a program for executing the method defined in claim 2.

13. A non-transitory computer-readable record medium storing a program for executing the method defined in claim 3.

14. A non-transitory computer-readable record medium storing a program for executing the method defined in claim 4.

15. A non-transitory computer-readable record medium storing a program for executing the method defined in claim 5.

16. A non-transitory computer-readable record medium storing a program for executing the method defined in claim 6.

17. A non-transitory computer-readable record medium storing a program for executing the method defined in claim 7.

18. A non-transitory computer-readable record medium storing a program for executing the method defined in claim 8.

19. A non-transitory computer-readable record medium storing a program for executing the method defined in claim 9.

* * * * *